United States Patent
Akers, Jr.

[11] Patent Number: 5,827,749
[45] Date of Patent: *Oct. 27, 1998

[54] LIGAND ASSAY METHOD

[75] Inventor: Raymond F. Akers, Jr., Sewell, N.J.

[73] Assignee: Akers Laboratories, Inc., Thorofare, N.J.

[*] Notice: The term of this patent shall not extend beyond the expiration date of Pat. No. 5,231,035.

[21] Appl. No.: 730,522

[22] Filed: Oct. 11, 1996

Related U.S. Application Data

[62] Division of Ser. No. 248,835, May 25, 1994, Pat. No. 5,565,366, which is a continuation of Ser. No. 588,670, Sep. 26, 1990, abandoned.

[51] Int. Cl.$^6$ .................................................. G01N 33/546
[52] U.S. Cl. .................. 436/534; 435/4; 435/5; 435/7.32; 435/7.9; 435/970; 436/523; 436/531; 436/533; 436/535; 436/538; 436/807; 436/825
[58] Field of Search ................................. 422/56, 58, 61, 422/73, 70, 99, 101, 102; 435/4, 5, 7.9, 28, 810, 970, 7.32; 436/518, 523, 531, 525, 533, 534, 535, 161, 162, 165, 169, 805, 807, 825, 538

[56] References Cited

U.S. PATENT DOCUMENTS

| | | | |
|---|---|---|---|
| 4,033,720 | 7/1977 | Silvestri | 436/162 |
| 4,043,989 | 8/1977 | Schneider et al. | 260/112 |
| 4,108,974 | 8/1978 | Wegfahrt et al. | 424/1 |
| 4,157,299 | 6/1979 | Landowne | 436/162 |
| 4,196,167 | 4/1980 | Olsen | 422/102 |
| 4,226,747 | 10/1980 | Roncari | 260/8 |
| 4,235,601 | 11/1980 | Deutsch et al. | 422/56 X |
| 4,243,654 | 1/1981 | Schneider et al. | 424/12 |
| 4,256,834 | 3/1981 | Zuk et al. | 435/7 |
| 4,292,038 | 9/1981 | Kondo et al. | 23/230 |
| 4,366,241 | 12/1982 | Tom et al. | 435/7 |
| 4,419,453 | 12/1983 | Dorman et al. | 436/534 |
| 4,444,880 | 4/1984 | Tom | 435/7 |
| 4,454,233 | 6/1984 | Wang | 436/525 |
| 4,459,361 | 7/1984 | Gefter | 422/61 |
| 4,471,559 | 9/1984 | Opp | 422/61 |
| 4,542,103 | 9/1985 | Adams | 436/534 |
| 4,552,839 | 11/1985 | Gould et al. | 422/56 |
| 4,596,695 | 6/1986 | Cottingham | 422/101 |
| 4,624,929 | 11/1986 | Ullman | 436/162 |
| 4,703,018 | 10/1987 | Craig et al. | 436/518 |
| 4,727,022 | 2/1988 | Skold et al. | 435/7 |
| 4,738,932 | 4/1988 | Yabusaki | 436/511 |
| 4,753,775 | 6/1988 | Ebersole et al. | 422/81 |
| 4,756,828 | 7/1988 | Litman et al. | 436/162 |

(List continued on next page.)

FOREIGN PATENT DOCUMENTS

| | | |
|---|---|---|
| A-55287/86 | 3/1986 | Australia . |
| 0120602 | 10/1984 | European Pat. Off. . |
| 0 280 559 | 8/1988 | European Pat. Off. . |
| 0 293 779 | 12/1988 | European Pat. Off. . |
| 0 297 292 | 1/1989 | European Pat. Off. . |
| 0 310 862 | 4/1989 | European Pat. Off. . |
| 0 310 872 | 4/1989 | European Pat. Off. . |
| 0 291 194 B1 | 2/1994 | European Pat. Off. . |
| 3511012 A1 | 10/1986 | Germany . |
| 8808534 | 3/1988 | WIPO .................. 436/525 |

OTHER PUBLICATIONS

Masson, et al., *Methods in Enzymology*, 1981, 74, 106–139.

*Primary Examiner*—Carol A. Spiegel
*Attorney, Agent, or Firm*—Pennie & Edmonds LLP

[57] ABSTRACT

Methods for determining the presence of a ligand in a sample suspected to contain the ligand are provided, along with apparatus suitable for performing the methods. The methods depend upon a color visualization indicating the ligand's presence or absence in the sample. Preferred methods comprise contacting the sample with colored particles which bear on their surface a receptor specific for the ligand, passing the sample/particle mixture through a filter, and then analyzing the color of the filtrate. The presence of ligand in the sample is established where the color of the filtrate is substantially different from the color of the receptor-bearing particles.

22 Claims, 2 Drawing Sheets

U.S. PATENT DOCUMENTS

| | | | |
|---|---|---|---|
| 4,756,884 | 7/1988 | Hillman et al. | 422/73 |
| 4,775,515 | 10/1988 | Cotingham | 422/73 |
| 4,808,518 | 2/1989 | Dorsett et al. | 435/5 |
| 4,808,524 | 2/1989 | Snyder et al. | 435/36 |
| 4,812,414 | 3/1989 | Warren, III et al. | 436/533 |
| 4,824,230 | 4/1989 | Litt | 422/73 |
| 4,837,168 | 6/1989 | de Jaeger et al. | 436/533 |
| 4,847,199 | 7/1989 | Snyder et al. | 435/36 |
| 4,849,340 | 7/1989 | Oberhardt | 439/13 |
| 4,861,711 | 8/1989 | Friesen et al. | 436/7.9 |
| 4,943,522 | 7/1990 | Eisnger et al. | 422/101 |
| 4,960,691 | 10/1990 | Gordon et al. | 422/70 |
| 4,960,692 | 10/1990 | Lentrichia et al. | 435/7.92 |
| 4,981,786 | 1/1991 | Dafforn et al. | 435/7.9 |
| 4,999,285 | 3/1991 | Stiso | 436/162 |
| 5,077,198 | 12/1991 | Shih et al. | 435/7.9 |
| 5,079,142 | 1/1992 | Coleman et al. | 435/7.92 |
| 5,120,643 | 6/1992 | Ching et al. | 435/7.92 |
| 5,231,035 | 7/1993 | Akers, Jr. | 436/531 |
| 5,248,479 | 9/1993 | Parsons et al. | 422/58 |
| 5,565,366 | 10/1996 | Akers, Jr. | 436/534 |

LIGAND ASSAY METHOD

This application is a divisional application of U.S. Ser. No. 08/248,835, filed May 25, 1995, now U.S. Pat. No. 5,565,366, which is a continuation application of U.S. Ser. No. 07/588,670, filed Sep. 26, 1990, presently abandoned.

FIELD OF THE INVENTION

This invention relates to methods and products for detecting the presence of specific chemical compounds in a variety of materials. More particularly, this invention relates to methods and products for the detection of biologically important ligands by an accurate assay technique which is faster, simpler, and less expensive than those previously known in the art.

BACKGROUND OF THE INVENTION

A great deal of research has been directed to the development of accurate techniques for determining the presence of organic materials such as drugs, contaminants, pollutants, and the like in substances of interest such as food, soil, and bodily fluids. For example, pathological or other conditions in human beings and animals are often detected by performing immunoassays on samples of bodily fluids such as urine or blood serum. Immunoassays are based on the capacity of a first compound, known as a ligand, to recognize or bind a second compound, known as a receptor, having a specific spatial and/or polar organization. Typically, immunoassays are used for the detection of antibodies or antigens in bodily fluids.

Antigens are foreign substances which, when introduced into a higher animal, bring about the formation of antibodies which react with the antigens to initiate protection against infection or disease. The presence of an antigen or an antibody can be confirmed or determined by adding the corresponding antibody or the corresponding antigen to a sample of bodily fluid. The presence or absence of the antibody or antigen in the sample is usually established by detecting the occurrence or nonoccurrence of a reaction between the specific ligand receptor pair, which usually manifests itself by insolubility or agglutination.

Because most ligand/receptor pairs are detected only with difficulty, it is frequently necessary to use certain inert carrier moieties to facilitate their detection. For example, in most latex agglutination techniques the receptor is covalently bound to discrete latex particles having diameters on the order of about 0.01 to about 100 micrometers. These particles are cross-linked or otherwise aggregated by the complementary ligand. The agglutination of such particles into relatively large aggregates or clumps is then observed.

The different types of latex agglutination techniques presently known in the art may be categorized into three basic classes based upon the particular method employed for detecting ligand/particle aggregates. The techniques of the first class involve centrifugation. For example, U.S. Pat. No. 4,738,932 in the name of Yabusaki discloses a centrifugation technique which involves rotating an agglutination slide on a serological rotator and then using a magnifier to examine slide wells for agglutination.

The second class comprises techniques which detect aggregates by particle counting. For example, Masson, et al., *Methods in Enzymology,* 1982, 74, 106–139 disclose an immunoassay technique in which a complicated device which uses forward light scattering is employed to count unaggregated particles. Thus, both the centrifugation and particle counting techniques have the disadvantages of complicated, time-consuming procedures and expensive, highly specialized devices.

The techniques of the third class are those in which agglutination is detected visually. However, since the average human eye can only detect particles down to about 40 micrometers in diameter, most visual agglutination tests must produce relatively large aggregates which typically require an undesirably long time to form. U.S. Pat. No. 4,459,361 in the name of Gefter discloses a somewhat improved type of visual technique which involves visual detection of unaggregated particles rather than aggregated particles. In the technique according to Gefter, both the ligand and the receptor are separately immobilized on latex particles and then mixed with a sample of bodily fluid suspected to contain the ligand. According to Gefter, the ligand in the sample competes with the ligand-bearing particles for the receptor sites on the receptor-bearing particles. To the extent that the ligand contained in the sample binds to the receptor-bearing particles, the ligand-bearing particles fail to aggregate. Thus, when such a mixture is exposed to a filter having a controlled pore size there is a substantial increase in the amount of unaggregated, ligand-bearing particles which pass through the filter. It is the presence of these unaggregated particles which is then detected.

According to Gefter, the amount of unaggregated particles which pass through the filter is proportional to the amount of ligand in the sample. Further, Gefter states that the number of unaggregated particles is sufficient to be visible to the naked eye, and that this visibility can be enhanced by the selection of the size, color, optical density, or fluorescence of the particles.

However, the technique disclosed by Gefter has a number of serious shortcomings. For example, the technique requires that both ligand- and receptor-bearing particles be prepared, thus adding considerable time and expense. While Gefter asserts that the unaggregated, ligand-bearing particles can be detected with the naked eye, the provided examples do not detect such particles visually, but rather with sophisticated spectrophotometric devices.

Accordingly there exists a long-felt need for relatively simple, inexpensive techniques for the accurate detection of biologically important chemical compounds present in bodily fluids and in other sample fluids.

OBJECTS OF THE INVENTION

It is therefore one object of the present invention to provide methods and products for detecting the presence of chemical compounds in a variety of substances.

It is another object of this invention to provide methods and products for accurately detecting biologically important ligands.

It is still another object of this invention to provide methods and products for detecting biologically important ligands which are faster, simpler, and less expensive than those known in the art.

It is a further object of this invention to provide improved methods and products for performing latex agglutination immunoassays.

SUMMARY OF THE INVENTION

These and other objects are achieved by the present invention, which provides methods and apparatus for determining the presence of a ligand in a sample suspected to contain the ligand. The methods and apparatus depend upon a color visualization indicating the ligand's presence or absence in the sample. This color visualization does not require the use of complicated instrumentation or equipment. All color changes are readily detected by the naked human eye.

The preferred methods of this invention comprise forming a test mixture by contacting the sample with colored particles which bear on their surface receptors specific for the ligand. Thus, the particles have the capacity to form ligand/particle aggregates upon contacting the ligand. The test mixture is then passed through a filter having apertures which are larger than the particles but generally smaller than the aggregates, in-order to remove the aggregates from the filtrate. The color of the filtrate is then analyzed. The presence of ligand in the sample is established where the color of the filtrate is substantially different from the color of the receptor-bearing particles.

The present invention also provides assay plates and reaction cells suitable for performance of the methods disclosed. Preferred assay plates comprise a top member having a filter well and an observation well. The assay plates further comprise filter means adjacent the top member and extending across the filter well, wicking means adjacent the filter means and extending the length and width of the filter well and the observation well, and a bottom member adjacent the wicking means. In preferred embodiments, the top member, filter means, wicking means, and bottom member are held in position with an appropriately applied adhesive.

Reaction cells according to this invention comprise receptor-bearing particles. Preferably, the reaction cell is a pipette and the particles are colored and contained in a breakable vessel within the pipette. In certain other embodiments, the reaction cell further comprises a kill solution to inactivate all biologically active materials employed in performing the assay.

The methods generally can be performed more rapidly than other visually-detected immunoassays, as the relatively small aggregates which indicate the presence of ligand in the present invention form more rapidly than the larger particles required by prior art techniques. Also, the methods and apparatus are as complex, time-consuming manipulative steps nor expensive and complicated devices. Thus, the present methods and apparatus can conveniently be used by persons having little or no technical training.

DETAILED DESCRIPTION OF THE INVENTION

Figure 2:
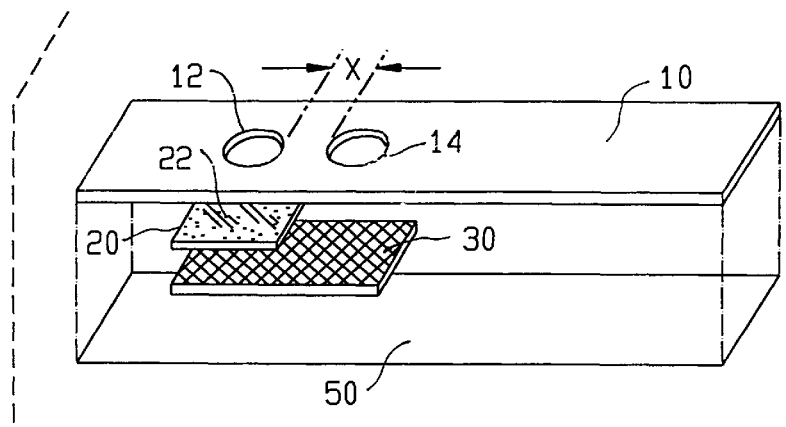
FIG. 2 is an exploded sectional view of an assay plate according to the present invention.
Figure 1:
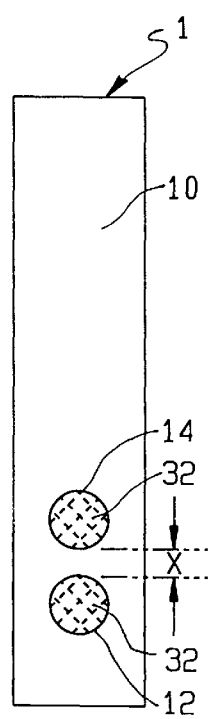
FIG. 1 is a top plan view of an assay plate according to the present invention.

The present invention provides a sensitive and accurate yet simple method for determining relatively low concentrations of a wide variety of ligands which may be present in various, sampled substances. The invention can be applied to detect virtually any ligand contained in a sample of bodily fluids, such as urine, serum, and plasma, derived from mammals, especially humans.

It will be appreciated that the term "ligand" denotes all constituents in bodily fluids, cell extracts, and tissue extracts for which there is present or can be formed an immunological reaction partner. Both antigens and antibodies are ligands according to this invention, as are amides, amino acids, peptides, proteins, lipoproteins, glycoproteins, sterols, steroids, lipoids, nucleic acids, enzymes, hormones, vitamins, polysaccharides, and alkaloids.

Representative examples of antigens are the "materials" set forth in U.S. Pat. No. 4,256,834 in the names of Zuk, et al., which is incorporated herein by reference. Antigens of interest include tetrahydrocannabinol and its metabolites, cocaine and its metabolites, morphine and other opiates, amphetamine, phencyclidine, barbiturates, steroids, rheumatoid factor, histoplasma, human chorionic gonadotropin, luteinizing hormone, follicle stimulating hormone, C reactive protein, and acid phosphate. Antigens of particular interest include the proteins derived from cultures of HIV-1 virus, cytomegalovirus, HIV-2 virus, hepatitis-B virus, hepatitis-C virus, herpes 1 and 2 virus, HTLV 1 virus, chlamydia virus, *Borrelia burgdorferi, Treponema pallidum, Neisseria gonorrhoeae, staphylococcus*, and the *streptococci* of groups A and B.

Preferred ligands according to this invention are those having more than one active site. Those skilled in the art will appreciate that the active site of a ligand is that portion that binds a receptor for the ligand. A preferred type of ligand having more than one binding site is an antibody for an antigen.

Particularly preferred ligands are the antibodies for the antigenic proteins derived from HIV-1 virus, cytomegalovirus, and *Borrelia burgdorferi*.

According to one aspect of the present invention, a sample suspected to contain a ligand of interest is contacted with particles which bear on their surface receptors specific for the ligand. Thus, receptor-bearing particles have the capacity to form ligand/particle aggregates upon contacting the ligand. The quantity of receptor-bearing particles contacted with the sample is preferably selected such that essentially all such receptor-bearing particles form aggregates when contacted with the sample suspected to contain the ligand.

The particles may be of any latices which are known or believed to be employable for latex agglutination, such as exemplified by the homopolymers and copolymers produced from styrene or its derivatives such as methylstyrene, ethylstyrene, and chlorostyrene, olefins such as ethylene and propylene, acrylic acid or its esters such as methyl acrylate and ethyl acrylate, methacrylic acid or its derivatives such as ethyl methacrylate, acrylonitrile, and acrylamide, dienes such as butadiene, chloroprene, and isoprene, vinyl chloride, vinylidine chloride, and vinyl acetate. The latices of homopolymers or copolymers made of styrene, chlorostyrene, acrylic acid, vinyltoluene, methyl methacrylate are advantageously used.

Other useful particles include carboxylated polystyrene, with or without reactive groups to facilitate reaction with the receptor, such as amino groups, thiol groups, carboxyl groups or other reactive groups. Butadiene/styrene copolymers such as carboxylated styrene butadiene or acrylonitrile butadiene styrene are also useful. Inorganic particles, such as silicas, clay, carbons such as activated charcoal, and other materials on which the receptor or ligand can be immobilized can be used in the present invention.

It is important that the particles are approximately the same diameter, so that they will easily pass through the same size filter aperture. The particles should have mean diameters of about 0.01 to about 100 micrometers, preferably about 0.01 to about 10 micrometers. More preferably the mean diameter of the particles is about 0.3 micrometers and the diameters of the particles do not vary from the mean by more than 30% preferably not by more than 15%.

The particles preferably have a visually recognizable color produced by the addition of dyes, pigments, or coatings. For example, the preparation of dyed polyacrylamide particles is disclosed in U.S. Pat. No. 4,108,974 in the names of Wegfahrt, et al., which is incorporated herein by reference. It is preferred that the color be relatively dark, preferably black or dark blue.

Preferred particles are the small, uniform diameter colored polystyrene latex spheres available in a variety of diameters from Bangs Laboratories (Carmel, IND.) and Seradyn, Inc. (Indianapolis, IND.).

The treatment of latex particles with a receptor corresponding to the ligand of interest can be effected by any of the methods known in the art. The treatment conditions will understandably vary to some degree depending upon the physicochemical properties of the latex particles, the ligand, and the receptor. In accordance with preferred embodiments, a receptor is covalently bound to a particle of defined dimensions, preferably a latex particle having a spherical shape and defined, uniform diameter. The receptor can be an antibody, an enzyme, or any protein or other material which specifically binds to the ligand of interest. It is preferred that the receptor be an antigen or an antibody. While it is preferred that the receptor be chemically bonded to the latex particles, the particles may alternatively be coated with a substance to which the receptor will adhere, so long as the coating does not interfere with the binding between the ligand and the receptor. The amounts of immobilized receptor and particles are preferably adjusted so that each of the receptorbearing particles will aggregate with one or more of the ligands when mixed together for a reasonable time.

The sample and the receptor-bearing particles may be contacted in a number of ways. In a preferred method, the sample is mixed with a solution which contains the particles and other reagents necessary to promote the agglutination reaction, forming a test mixture. An interval is permitted to pass which is sufficient for agglutination to occur or for aggregates to otherwise form. Alternatively, the sample can be passed through a substrate such as a glass membrane which contains the particles and other reagents necessary to promote the agglutination reaction. Where the sample contains ligand, aggregates and other moieties will be released from the substrate. The released aggregates and other moieties also constitute test mixtures according to this invention. The test mixture is then exposed to a filter having apertures which are larger than the particles but generally smaller than the clumps of ligand/particle aggregates which might have formed. The filter should have a defined pore size which is about 5 to about 15 times larger than the latex particle diameter, preferably about 10 to about 12 times larger, more preferably about 3 micrometers in diameter. It will be appreciated that-there may be some small variance in the diameters of the pores. Preferably, the pore diameters will not vary from the nominal diameter by more than 30%, preferably not by more than 15%.

The pore size of the filter is chosen to retain ligand/particle aggregates yet permit the passage of the relatively small aggregates which may be formed by non-specific agglutination. It will be appreciated that non-specific agglutination is the aggregation of receptor-bearing particles in the absence of ligand. The sensitivity of the assay should be adjusted to produce aggregates larger than the pore size, roughly 10 to 15 particles in diameter. Preferably, the filter will be an absolute channel membrane having pores of controlled diameter. Preferred controlled pore membranes are which comprise polycarbonate, such as those commercially available from the Poretics Corporation (Livermore, CA).

Once the mixture is filtered, the filtrate produced thereby is analyzed for the presence of particles which are unaggregated or non-specifically aggregated. While it will be appreciated that such analysis may be performed by any of the appropriate physical and/or chemical methods known in the art, such as centrifugation or particle counting, analysis of the filtrate is preferably performed by visually inspecting the filtrate to determine the presence therein of a recognizable color corresponding to the latex particles. Thus, where the proportions of receptor-bearing particles and ligand -have been carefully in the filtrate of a color corresponding to the particles indicates the absence of ligand in the sample, and the absence of such color in the filtrate indicates the presence of ligand in the sample. It is, of course, also possible to determine the quantity of ligand present in a sample in accordance with the present invention. A suitable quantitative system may be established by comparing the filtrate with one or more visual standards corresponding to known concentrations of colored particles in the filtrate. Such visual standards will be prepared from samples having known concentrations of ligand.

The present invention also provides apparatus suitable for implementing the described methods for ligand assay. In general, such apparatus comprise: filter means for filtering the mixture produced by contacting a sample suspected to contain a ligand with receptor-bearing particles which have the capacity to form ligand/particle aggregates upon contacting the ligand; as well as analysis means for determining the presence of the particles in the filtrate which passes through the filter.

A preferred apparatus for performing the methods of the present invention is an assay plate (1), examples of which are shown in FIGS. 1 through 4. The assay plates of this invention generally comprise: a substantially flat top member (10) of predetermined dimensions having a filter well (12) and an observation well (14); filter means (20) adjacent the top member and extending across the filter well; wicking means(30) adjacent the filter means and extending the length and width of the filter well and the observation well; and a substantially flat bottom member (50) having the approximate dimensions of the top member, adjacent the wicking means. It will be appreciated that analysis means comprises elements of the assay plates other than the filter means.

The top member preferably comprises a material which is substantially impermeable to aqueous solutions such as associated with human body. The top member preferably is cut or stamped from a rigid material and, thus, is able to impart some degree of support to the assay plate. It is preferred that the top member comprise polystyrene and have a length of about 100 millimeters, a width of about 20 millimeters, and a thickness of about 1.0millimeters.

The top member should be cut, stamped, or otherwise fabricated to have a filter well (12) and an observation well (14) extending though the entire thickness of the top member. Preferably, the filter well and the observation well are circular, but other shapes are possible. It is also preferred that the filter well and the observation well be a predetermined distance (X) from one another. Since there exists the possibility that some ligand/particles aggregates might not form clumps of sufficient diameter to be retained by the filter, the predetermined distance (X) is selected such that any ligand/particle aggregates which pass through the filter do not reach the observation window. Thus, the predetermined distance (X) will vary with the specific ligand, receptor, particle, and wicking means employed. It will generally be the case that the distance (X) varies in an inverse fashion with the capacity of the wicking means to retain aggregates.

The filter means (20) is preferably a filter as described above having apertures (22) which are larger than the particles but generally smaller than the clumps of ligand/particle aggregates. It is preferred that the filter means be a controlled pore polycarbonate membrane. While the filter means need only extend across the filter well, where the filter means is transparent or nearly transparent, such as where the filter means is a controlled pore polycarbonate membrane, the filter means preferably also extends across the observation well, as in FIG. 3.

Adjacent the filter means is the wicking means (30). The wicking means is preferably positioned in close physical contact with the filter means such that filtrate flows vertically into the wicking means and migrates horizontally from a position beneath the filter well to a position beneath the observation well. While the filter means need only extend the length of the filter well and the observation well, the wicking means is preferably somewhat longer, as in FIG. 3. The filter means and the wicking means are preferably attached to one another with a porous adhesive, such as the adhesive available from Adhesive Research Company (Glen Rock, PA) under the tradename ARcare Porous. It is preferred that the wicking means comprise non-woven fibers of glass or natural or synthetic polymeric materials, preferably polyester. The composition and arrangement of the fibers in the wicking means are selected such that the aggregates and the particles migrate thereon at different rates. Preferably the particles migrate faster. It is also preferred that the wicking means have an embossed or otherwise formed visually recognizable pattern, such as a crosshatch pattern (32), to facilitate the visual detection of color at the observation well.

The bottom member (50) is adjacent the wicking means and preferably comprises a material which is substantially impermeable to aqueous solutions. The bottom member preferably is cut or stamped to have the approximate width and length of the top member. The top member and/or the bottom member should serve to support the assay plate. Thus, where the top member provides adequate support, the bottom member may comprise a relatively non-rigid material, such as a vinyl polymer. The bottom member is preferably physically attached to the other components of the assay plate with an adhesive. Since many suitable adhesives impair the wicking properties of the wicking means, preferred assay plates have a barrier (40) such as a thin polyethylene film at least as long as the wicking means and positioned between the wicking means and the adhesive-bearing bottom member.

Figure 4:
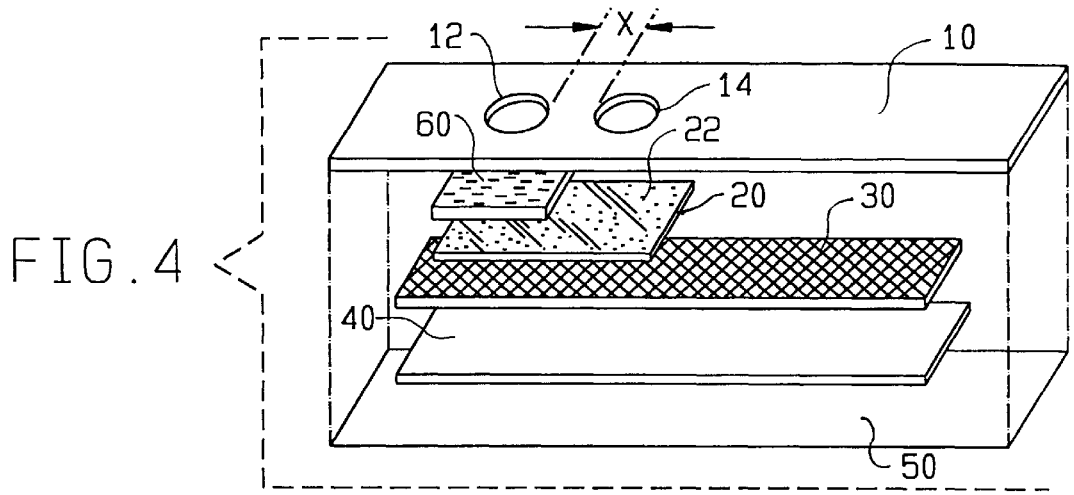
FIG. 4 is an exploded sectional view of an assay plate according to the present invention having a receptor-bearing substrate beneath the filter well.

The assay plates of this invention optionally also comprise substrate (60), such as a glass membrane, containing receptor-bearing particles and other reagents necessary to promote the agglutination reaction. Such a substrate is to be employed where the sample is to be applied directly into the filter well, rather than pre-mixed with a solution containing the receptor-bearing particles. The substrate should be positioned between the top member and the filter means and should extend across the filter well, as shown in FIG. 4.

Figure 5:
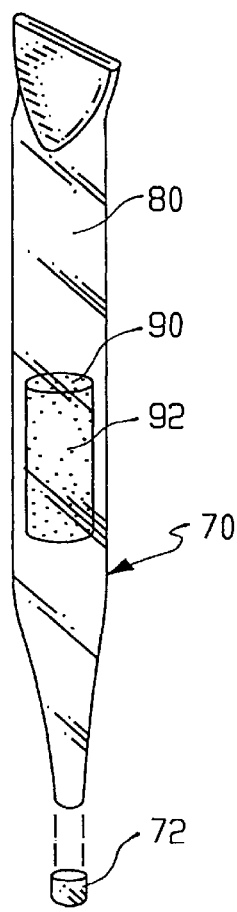
FIG. 5 is a perspective view of a reaction cell according to the present invention.

The present invention additionally provides reaction cells for use in contacting a sample with receptor-bearing particles. A preferred type of reaction cell (70) is depicted in FIG. 5. One element of reaction cells according to this invention is a container (80) in which receptor-bearing particles may be contacted with a sample suspected to contain a ligand. Such containers may have a variety of shapes. However, a preferably-shaped container is a pipette, such as shown in FIG. 5. It will be appreciated that containers having an open end preferably further comprise a cap (72) for containing the sample and receptorbearing particles. Preferred containers are disposable and comprise any of the relatively inexpensive, substantially transparent synthetic polymers known in the art. Suitable transparent pipette-shaped containers are available from Franklin, Inc. (Franklin, N.J.). Within preferred reaction cells are breakable-vessels (90) containing the receptor-bearing particles (92). The breakable vessel may comprise glass or some synthetic polymer, so long as the material employed has sufficient structural integrity to contain the particles securely until the particles are to be contacted with the sample, at which time the vessel is broken or ruptured by applied force. Where a reaction cell contains a breakable vessel, it is necessary that the container comprise a relatively supple material through which such rupturing force may be applied to the breakable vessel.

Preferred reaction cells further comprise a kill solution. It is intended that the term "kill solution" denote any solution having the capacity to biologically inactivate the moieties—such as ligands, receptors, or samples—employed in performing a ligand assay. Solutions comprising ethanol, formaldehyde, glutaraldehyde, iodophors, or oxidizing bleaches provide examples of kill solutions according to this invention. It is preferred that kill solutions comprise oxidizing bleaches such as sodium hypochlorite. The kill solution is preferably contained in a compartment (100) at one end of the container and separated therefrom by a rupturable membrane (102). Alternatively, the kill solution is contained in a breakable vessel (110) located within the container. The membrane or vessel comprises a material which has sufficient structural integrity to contain the kill solution securely until broken or ruptured by applied force. The kill solution is then released and contacted with any biologically active substances located in the container or on the assay plate, usually upon the completion of an assay.

The present invention also provides kits useful for ligand assay. Certain of these kits consist essentially of the receptor-bearing particles and the filter means described above. Other kits comprise an assay plate and a reaction cell.

Additional objects, advantages, and novel features of this invention will become apparent to those skilled in the art upon examination of the following examples thereof, which are not intended to be limiting, wherein parts and percents are by weight unless otherwise indicated.

EXAMPLE 1

Purified HIV-1 antigenic proteins were passively adsorbed to dyed polystyrene latex particles having a mean diameter of about 0.3 micrometers in a 0.1 molar glycine buffered saline (GBS) solution (pH =8.0) for about 12 hours at 4° C. The particles were then centrifuged and washed with a GBS solution comprising 0.1%bovine serum albumin (BSA).

The particles were then added to GBS solution along with certain other moieties which are believed to optimize the speed and sensitivity of the agglutination reaction to yield a solution comprising: the particles (0.5%); BSA (0.1%); polyethylene glycol (6%); polyvinylpyrrolidone (1%); sodium azide (0.5%) and free HIV-1 antigenic protein (1.0 picograms per milliliter )

EXAMPLE 2

Purified antigenic proteins isolated from *Borrelia burgdorferi* cultures were passively adsorbed to dyed polystyrene latex particles having a mean diameter of about 0.3 micrometers in a 0.1 molar phosphate buffered saline (PBS) solution (pH =7.2) for about 12 hours at 4° C. The particles were then centrifuged and washed with a PBS solution comprising 0.1% BSA.

The particles were then added to PBS solution along with certain other moieties which are believed to optimize the speed and sensitivity of the agglutination reaction to yield a solution comprising: BSA (2%); the particles (0.5%); polyethylene glycol (6%); ethylenediamine tetraacetic acid (EDTA) (1%); and sodium azide (0.5%).

EXAMPLE 3

Purified antigenic proteins isolated from cytomegaloviral cultures were passively adsorbed to dyed polystyrene latex particles having a mean diameter of about 0.3 micrometers in a 0.1molar GBS solution (pH =7.0) for about 12 hours at 4° C.

The particles were then added to GBS solution along with certain other moieties which are believed to optimize the speed and sensitivity of the agglutination reaction to yield a solution comprising: the particles (0.5%); BSA (0.1%); polyethylene glycol (6%); sodium chloride (1.5 molar); -and sodium azide (0.5%).

EXAMPLE 4

Figure 3:
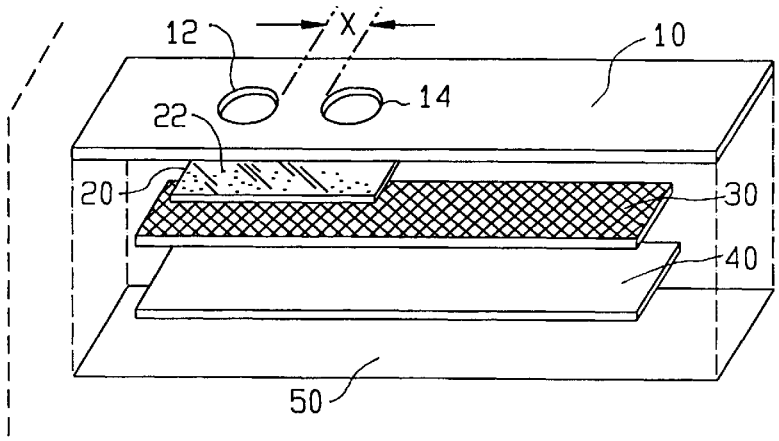
FIG. 3 is an exploded sectional view of a preferred assay plate according to the present invention having a barrier between the wicking means and the bottom member.

A 100 microliter sample of human serum known to contain antibodies to HIV-1 virus was drawn into a pipette-shaped reaction cell such as shown in FIG. 5. The breakable vessel within the reaction cell contained 200 microliters of the solution prepared in Example 1. The reaction cell was closed by replacing its cap and the breakable vessel was ruptured by squeezing it between the thumb and index finger. The reaction cell was then shaken gently. After about 10–30 seconds, the cap was removed and a few drops of the dark blue sample/particle mixture were placed in the filter well of an assay plate such as shown in FIG. 3. The assay plate had a polycarbonate membrane with controlled pores of about 3micrometers and a polyester wicking layer. The distance (X) between the filter well and the observation well was 0.25 inches.

After about 1–3 minutes, dark blue clumps of particle/ligand aggregates were observed in the filter well. No dark blue color was observed in the observation well.

Figure 6:
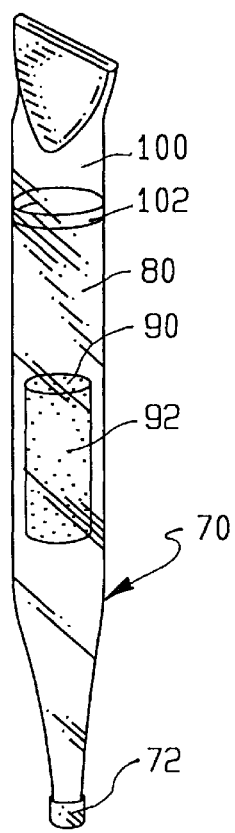
FIG. 6 is a perspective view of a reaction cell according to the present invention comprising kill solution in a compartment.
Figure 7:
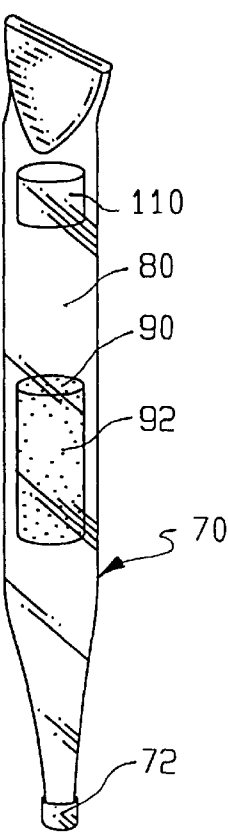
FIG. 7 is a perspective view of a reaction cell according to the present invention comprising kill solution in a breakable vessel.

It will be appreciated that had a reaction cell such as shown in FIG. 6 or FIG. 7 been employed instead of the reaction cell of FIG. 5, biologically active substances could next be inactivated by breaking or rupturing the membrane (102) or vessel (110) and contacting the released kill solution with the container and/or assay plate.

EXAMPLE 5

The procedure of Example 4 was repeated, except that a sample of serum known to not contain antibodies to HIV-1 virus was used.

After about 1 minute, only a few clumps of particle/ligand aggregates were observed in the filter well. A dark blue color was observed in the wick material beneath the observation well.

EXAMPLE 6

The procedure of Example 4 was repeated using a sample of human serum which contained antibodies to *Borrelia burgdorferi* in place of antibodies to HIV-1 virus. The solution from Example 2 was employed in place of the solution of Example 1.

After about 1–3 minutes, dark blue clumps of particle/ligand aggregates were observed in the filter well. No dark blue color was observed in the observation well.

EXAMPLE 7

The procedure of Example 6 was followed, except that a sample of serum known to not contain antibodies to *Borrelia burgdorferi* was used.

After about 1 minute, only a few clumps of particle/ligand aggregates were observed in the filter-well. A dark blue color was observed in the wick material beneath the observation well.

EXAMPLE 8

The procedure of Example 4 was repeated using a sample of human serum which contained antibodies to cytomegalovirus in place of antibodies to HIV-1 virus. The solution from Example 3 was employed in place of the solution of Example 1.

After about 1–3 minutes, dark blue clumps of particle/ligand aggregates were observed in the filter well. No dark blue color was observed in the observation well.

EXAMPLE 9

The procedure of Example 8 was followed, except that a sample of serum known to not contain antibodies to cytomegalovirus was used.

After about 1 minute, only a few clumps of particle/ligand aggregates were observed in the filter well. A dark blue color was observed in the wick material beneath the observation well.

EXAMPLE 10

A 200 microliter sample of human serum known to contain antibodies to HIV-1 virus was pipetted into the filter well of an assay plate such as shown in FIG. 4. The assay plate had a glass membrane substrate (60) which had been saturated with the solution prepared in Example 1. The assay plate had a polycarbonate membrane with controlled pores of about 3 micrometers and a polyester wicking layer. The distance (X) between the filter well and the observation well was 0.25 inches.

After about 1–3 minutes, dark blue clumps of particle/ligand aggregates were observed in the filter well. No dark blue color was observed in the observation well.

EXAMPLE 11

The procedure of Example 10 was followed, except that a sample of serum known to not contain antibodies to HIV-1 virus was used.

After about 1 minute, no clumps of particle/ligand aggregates were observed in the filter well. A dark blue color was observed in the wick material beneath the observation well.

What is claimed is:

1. A method for determining the presence of a ligand in a sample suspected to contain the ligand, comprising:

forming a test mixture by containing the sample with particulate material, said particulate material being approximately the same diameter from about 0.01 to about 100 micrometers which bears on its surface receptors specific for the ligand and which forms aggregates upon contacting the ligand in the presence of an optimizing agent, effective to optimize speed and sensitivity of the aggregation reaction;

passing the test mixture through a filter means comprising apertures which are larger than the receptor-bearing particulate material but smaller than the aggregates, thereby producing a filtrate;

passing said filtrate through a wicking means adjacent and in fluid communication with the filter means, said wicking means consisting essentially of non-woven fibers of glass or synthetic polymeric material for effecting separation of any non-specifically aggregated receptor-bearing particulate material and/or any unaggregated receptor-bearing particulate material, wherein any unaggregated receptor-bearing particulate material migrates horizontally through said wicking means at a rate faster than said ligand/receptor-bearing particulate material, the presence of non-specifically aggregated or unaggregated receptor-bearing particulate material in the filtrate indicating the absence of the ligand in the sample and the absence of non-specifically aggregated or unaggregated receptor-bearing particulate material in the filtrate indicating the presence of the ligand in the sample.

2. The method of claim 1 wherein the ligand has more than one active site.

3. The method of claim 1 wherein the ligand is an antigen.

4. The method of claim 1 wherein the ligand is an antibody to an antigen.

5. The method of claim 1 wherein the ligand is an antibody to an antigen selected from the group consisting of HIV-1virus, cytomegalovirus, and *Borrelia burgdorferi*.

6. The method of claim 1 wherein the sample comprises a mammalian bodily fluid.

7. The method of claim 1 wherein the sample comprises a human bodily fluid.

8. The method of claim 1 wherein the receptor-bearing particulate material has a mean diameter of about 0.3 micrometers.

9. The method of claim 1 wherein the receptor-bearing particulate material comprises latex.

10. The method of claim 1 wherein the receptor-bearing material particulate comprises polystyrene.

11. The method of claim 1 wherein the receptor-bearing particulate material has a visually recognizable color which can be ascertained by the unaided eye.

12. The method of claim 1 wherein the contacting step is performed by contacting the sample with a solution which contains the receptor-bearing particulate material.

13. The method of claim 1 wherein the contacting step is performed in a reaction cell.

14. The method of claim1 wherein the contacting step is performed by contacting the sample with a substrate which contains the receptor-bearing particulate material.

15. The method of claim 1 wherein the filter means comprises a controlled pore membrane.

16. The method of claim 1 wherein the filter means comprises polycarbonate.

17. The method of claim 1 wherein the apertures are from about 5 to about 15 times larger than the receptor-bearing particulate material.

18. The method of claim 1 wherein the apertures are from about 10to about 12 times larger than the receptor-bearing particulate material.

19. The method of claim 1 wherein the apertures are about 3 micrometers in diameter.

20. The method of claim 11 wherein the analyzing step comprises visually determining the color of the filtrate.

21. The method of claim 11 wherein the analyzing step comprises visually comparing the appearance of the filtrate with a visual standard corresponding to a known concentration of the receptor-bearing particulate material.

22. The method of claim 1 further comprising contacting the filtrate with a solution effective to inactive biological material present in the filtrate.

* * * * *